US012646616B2

(12) United States Patent
Baba et al.

(10) Patent No.: US 12,646,616 B2
(45) Date of Patent: Jun. 2, 2026

(54) PATIENT MONITORING SYSTEM

(71) Applicant: Sony Group Corporation, Tokyo (JP)

(72) Inventors: Hiroyasu Baba, Tokyo (JP); Takanori Fukazawa, Tokyo (JP); Minori Takahashi, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 275 days.

(21) Appl. No.: 18/555,270

(22) PCT Filed: Jan. 28, 2022

(86) PCT No.: PCT/JP2022/003254
§ 371 (c)(1),
(2) Date: Oct. 13, 2023

(87) PCT Pub. No.: WO2022/224524
PCT Pub. Date: Oct. 27, 2022

(65) Prior Publication Data
US 2024/0127948 A1     Apr. 18, 2024

(30) Foreign Application Priority Data
Apr. 22, 2021     (JP) ................................. 2021-072361

(51) Int. Cl.
*G16H 40/67*          (2018.01)
*A61B 5/00*           (2006.01)
*G16H 40/20*          (2018.01)

(52) U.S. Cl.
CPC ........... *G16H 40/67* (2018.01); *A61B 5/0013* (2013.01); *G16H 40/20* (2018.01)

(58) Field of Classification Search
CPC ........ G16H 40/67; G16H 40/20; G16H 30/40; G16H 50/20; A61B 5/0013
See application file for complete search history.

(56) References Cited

U.S. PATENT DOCUMENTS

2011/0317871 A1*   12/2011   Tossell ................... G06V 40/23
                                                           382/103
2019/0287682 A1    9/2019   Van Zon et al.
(Continued)

FOREIGN PATENT DOCUMENTS

JP          2008529328 A      7/2008
JP          2009-233042 A    10/2009
(Continued)

OTHER PUBLICATIONS

International Search Report and Written Opinion mailed on Apr. 12, 2022, received for PCT Application PCT/JP2022/003254, filed on Jan. 28, 2022, 11 pages including English Translation.

*Primary Examiner* — Carl H Layno
*Assistant Examiner* — Aya Ziad Bakkar
(74) *Attorney, Agent, or Firm* — XSENSUS LLP

(57)          ABSTRACT
A patient monitoring system that includes: an estimation unit that inputs vital information indicating a vital sign of a patient and video analysis information obtained by analyzing a video showing the patient to a first learning model to estimate a state of the patient; and a monitoring unit that monitors a state of the patient on the basis of an estimation result by the estimation unit. The present technology can be applied to, for example, a monitoring system provided in an Intensive Care Unit (ICU).

20 Claims, 13 Drawing Sheets

(56)                    References Cited

U.S. PATENT DOCUMENTS

| | | | |
|---|---|---|---|
| 2021/0015376 A1 | 1/2021 | Kim | |
| 2021/0030276 A1 * | 2/2021 | Li | ........................ G06N 3/0464 |

FOREIGN PATENT DOCUMENTS

| | | | | |
|---|---|---|---|---|
| JP | 2019-532390 A | 11/2019 | | |
| JP | 2020500570 A | 1/2020 | | |
| JP | 6697622 B1 | 5/2020 | | |
| JP | 2020-154630 A | 9/2020 | | |
| JP | 2021-508401 A | 3/2021 | | |
| JP | 2023035988 A | 3/2023 | | |
| WO | WO-2013166341 A1 * | 11/2013 | ............ | G16H 80/00 |
| WO | WO-2019102521 A1 * | 5/2019 | ............ | G08B 25/04 |
| WO | 2019/186955 A1 | 10/2019 | | |
| WO | WO-2019223796 A1 | 11/2019 | | |
| WO | 2020/158717 A1 | 8/2020 | | |
| WO | 2020/203015 A1 | 10/2020 | | |
| WO | 2021/020198 A1 | 2/2021 | | |
| WO | WO-2021064985 A1 | 4/2021 | | |

* cited by examiner

FIG. 11

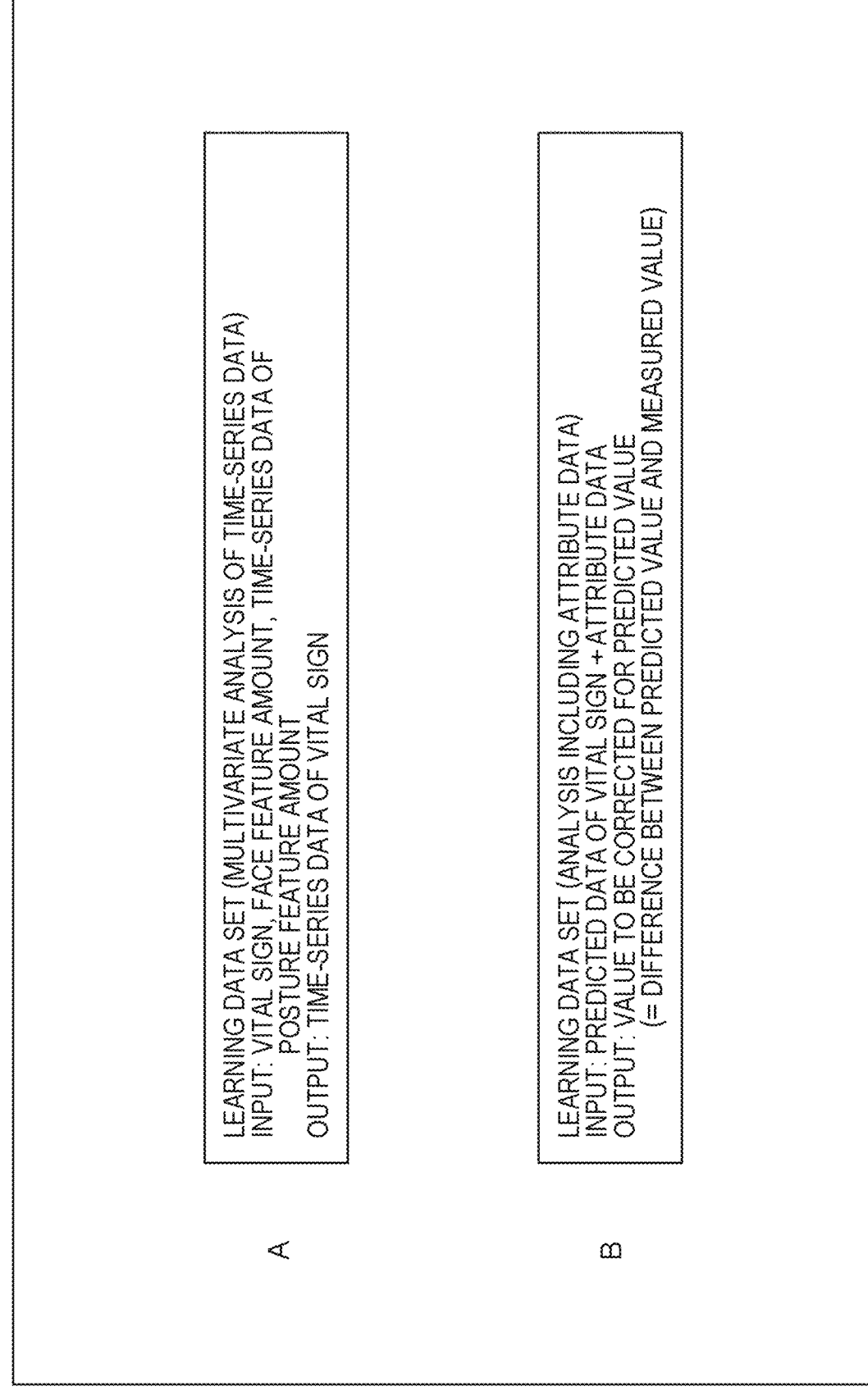

A

LEARNING DATA SET (MULTIVARIATE ANALYSIS OF TIME-SERIES DATA)
INPUT: VITAL SIGN, FACE FEATURE AMOUNT, TIME-SERIES DATA OF
        POSTURE FEATURE AMOUNT
OUTPUT: TIME-SERIES DATA OF VITAL SIGN

B

LEARNING DATA SET (ANALYSIS INCLUDING ATTRIBUTE DATA)
INPUT: PREDICTED DATA OF VITAL SIGN + ATTRIBUTE DATA
OUTPUT: VALUE TO BE CORRECTED FOR PREDICTED VALUE
        (= DIFFERENCE BETWEEN PREDICTED VALUE AND MEASURED VALUE)

*FIG. 13*

PATIENT MONITORING SYSTEM

CROSS-REFERENCE TO RELATED APPLICATIONS

The present application is based on PCT filing PCT/JP2022/003254, filed Jan. 28, 2022, which claims priority from Japanese Patent Application No. 2021-072361, filed Apr. 22, 2021, the entire contents of each are incorporated herein by reference.

TECHNICAL FIELD

The present technology relates to a patient monitoring system, and more particularly, to a patient monitoring system capable of appropriately monitoring a condition of a patient.

BACKGROUND ART

In medical settings, the condition of a patient may suddenly change. In an ICU, many patients are in a critical condition of life or in a post-operative condition, and the patient's condition is particularly likely to suddenly change. Therefore, a method for appropriately monitoring a patient is required.

For example, Patent Document 1 describes that a monitor screen displayed on a biological monitor is monitored, and a time at which an abnormality has occurred is displayed in an emphasized manner.

CITATION LIST

Patent Document

Patent Document 1: Japanese Patent Application Laid-Open No. 2009-233042

SUMMARY OF THE INVENTION

Problems to be Solved by the Invention

By the way, doctors and nurses do not grasp the patient's condition only by looking at the change in vital signs. Doctors or nurses sense a sign of a sudden change in abnormality or condition of a patient by empirically feeling uncomfortable by looking at the appearance of a patient together with a change in vital signs.

The present technology has been made in view of such a situation, and is intended to appropriately monitor the state of a patient.

Solutions to Problems

A patient monitoring system according to one aspect of the present technology includes: an estimation unit that inputs vital information indicating a vital sign of a patient and video analysis information obtained by analyzing a video showing the patient to a first learning model to estimate a state of the patient; and a monitoring unit that monitors a state of the patient on the basis of an estimation result by the estimation unit.

In one aspect of the present technology, vital information indicating a vital sign of a patient and video analysis information obtained by analyzing a video showing the patient are input to a first learning model, a state of the patient is estimated, and the state of the patient is monitored on the basis of an estimation result.

BRIEF DESCRIPTION OF DRAWINGS

FIG. 11 is a diagram illustrating an example of a learning data set of a learning model used for each analysis.

FIG. 13 is a block diagram illustrating a configuration example of hardware of a computer.

MODE FOR CARRYING OUT THE INVENTION

Modes for carrying out the present technology will be described below. The description will be made in the following order.

1. Patient monitoring system
2. Configuration of information processing apparatus
3. Operation of information processing apparatus
4. Modifications

1. Patient Monitoring System

Figure 1:
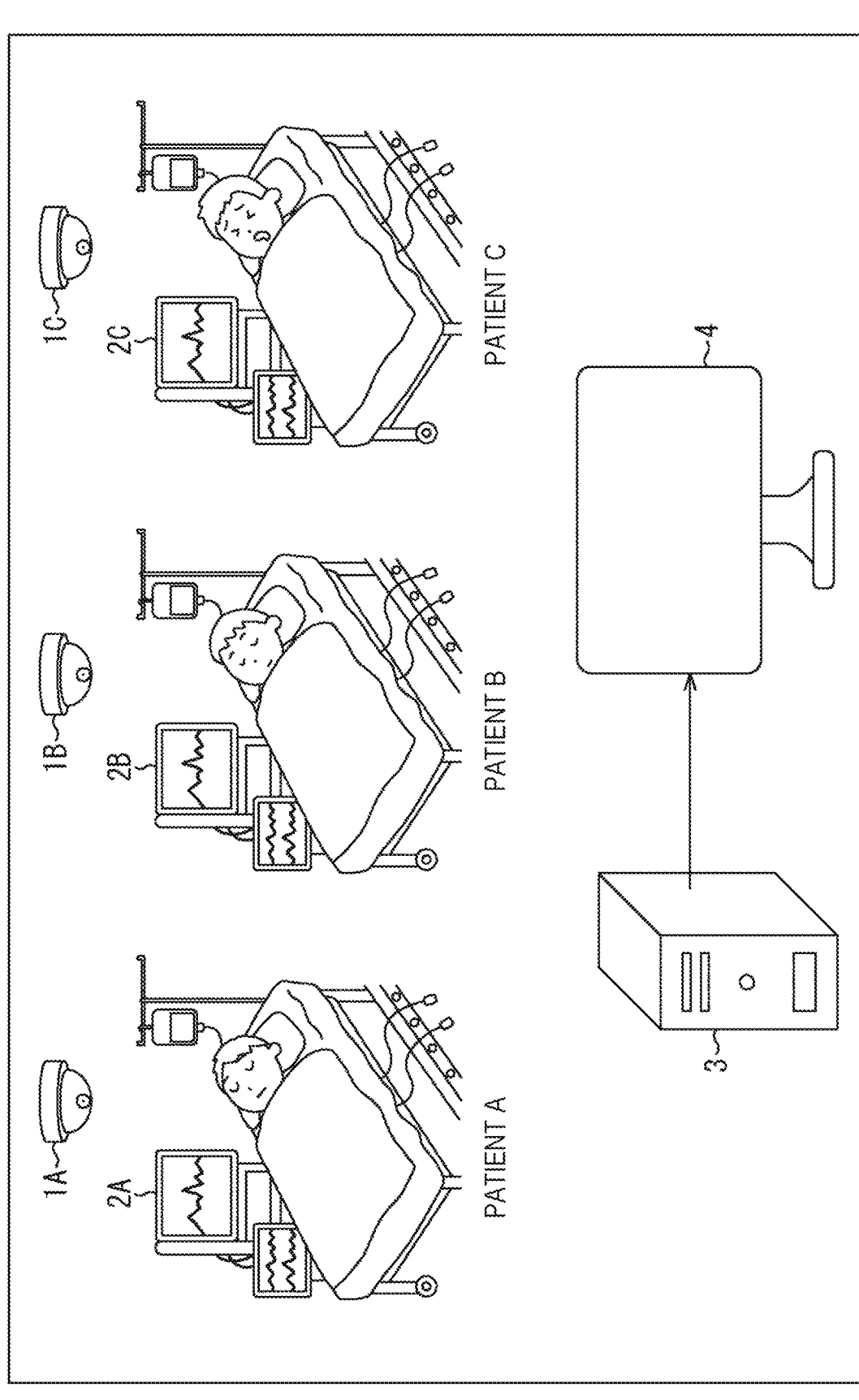
FIG. 1 is a diagram illustrating an embodiment of a patient monitoring system to which the present technology is applied.

FIG. 1 is a diagram illustrating an embodiment of a patient monitoring system to which the present technology is applied.

The patient monitoring system is a system that performs abnormality detection and sudden change prediction of a patient by performing analysis using an appearance feature amount obtained from a video showing the patient, in addition to patient vital sign data, diagnostic data, and attribute data. Results of abnormality detection and sudden change prediction are provided to the medical practitioner. The medical practitioner includes a doctor and a nurse.

The patient monitoring system in FIG. 1 is configured by connecting cameras 1A to 1C and medical devices 2A to 2C to an information processing apparatus 3 via wired or wireless communication. A monitor 4 is also connected to the information processing apparatus 3. Each device constituting the patient monitoring system is installed in, for example, an intensive care unit (ICU). In the example of FIG. 1, three beds used by patients A to C are installed in the ICU. Note that the cameras 1A to 1C and the medical devices 2A to 2C may be connected to the information processing apparatus 3 via a network. Furthermore, the cameras 1A to 1C and the medical devices 2A to 2C may be connected to the information processing apparatus 3 via an IP converter that converts the communication protocol into a predetermined communication protocol (for example, Internet Protocol (IP)). The IP converter includes an information processing circuit including a CPU and a memory.

The cameras 1A to 1C are configured as, for example, pan-tilt-zoom cameras capable of changing an imaging direction and an angle of view. The cameras 1A to 1C perform imaging and acquire videos showing the respective patients A to C. For example, RGB videos are acquired by the cameras 1A to 1C as videos showing the respective patients A to C. Note that, hereinafter, in a case where it is not necessary to distinguish the cameras 1A to 1C, the cameras 1A to 1C are simply referred to as a camera 1. The same applies to a plurality of other devices provided.

The medical devices 2A to 2C detect the vital signs of the respective patients A to C and acquire time-series data of the vital signs for a predetermined period as vital sign data (vital information).

For example, one camera 1 and one medical device 2 are provided for each patient as devices for each patient. In FIG. 1, three cameras 1 and three medical devices 2 are provided in the ICU, but actually, a number of cameras 1 and medical devices 2 corresponding to the number of patients and the number of beds are provided in the ICU.

The information processing apparatus 3 is an apparatus that performs abnormality detection and sudden change prediction of a patient and monitors a state of the patient. The information processing apparatus 3 acquires various data from devices and other systems in the ICU, other systems in the hospital, and the like.

Figure 2:
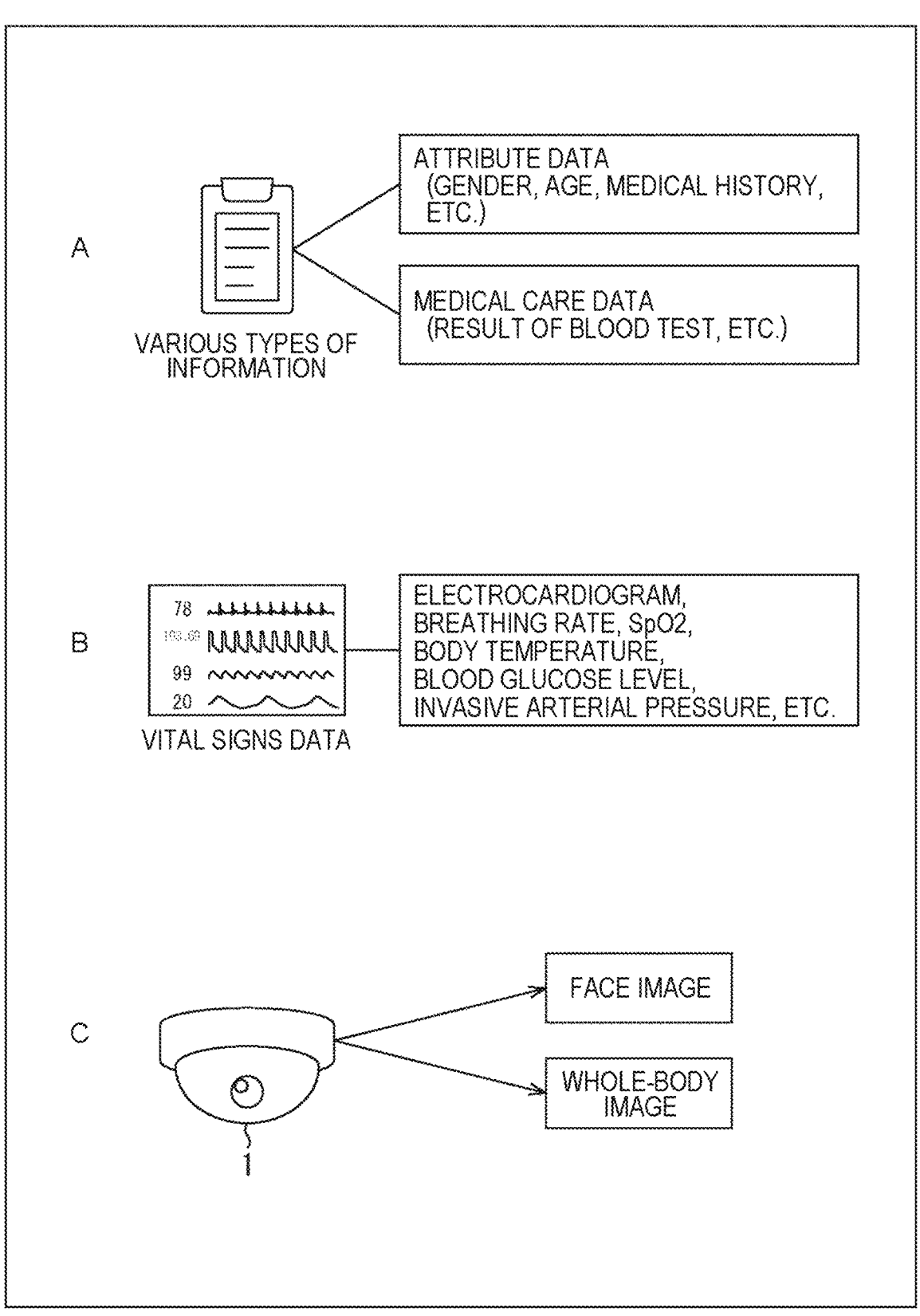
FIG. 2 is a diagram illustrating an example of data acquired by an information processing apparatus.

FIG. 2 is a diagram illustrating an example of data acquired by the information processing apparatus 3.

As illustrated in A of FIG. 2, attribute data indicating the gender, age, medical history, and the like of the patient, and medical care data indicating the result of the blood test, and the like are acquired from another system in the ICU or another system in the hospital. The medical care data is, for example, time-series data of a result of the blood test performed every predetermined period.

As illustrated in B of FIG. 2, time-series data such as an electrocardiogram, a breathing rate, SpO2, a body temperature, a blood glucose level, and an invasive arterial pressure is acquired from the medical device 2 as vital signs data.

As illustrated in C of FIG. 2, a face image showing the face of the patient and a whole-body image showing the entire body of the patient are acquired from the camera 1. A frame image constituting a video showing the patient is acquired as a face image and a whole-body image.

The information processing apparatus 3 in FIG. 1 extracts the appearance feature amount of the patient from the face image and the whole-body image acquired from the camera 1. The information processing apparatus 3 estimates the state of the patient by performing analysis on the basis of the appearance feature amount, the attribute data, the medical care data, and the vital signs data. Furthermore, the information processing apparatus 3 also records appearance feature amounts, medical care data, and vital signs data.

The monitor 4 displays a list of the video, the vital signs data, the estimation result of the state of the patient, and the like for each of the patients A to C, and displays a list of the video, the vital signs data, the estimation result of the state, and the like for one patient.

Figure 3:
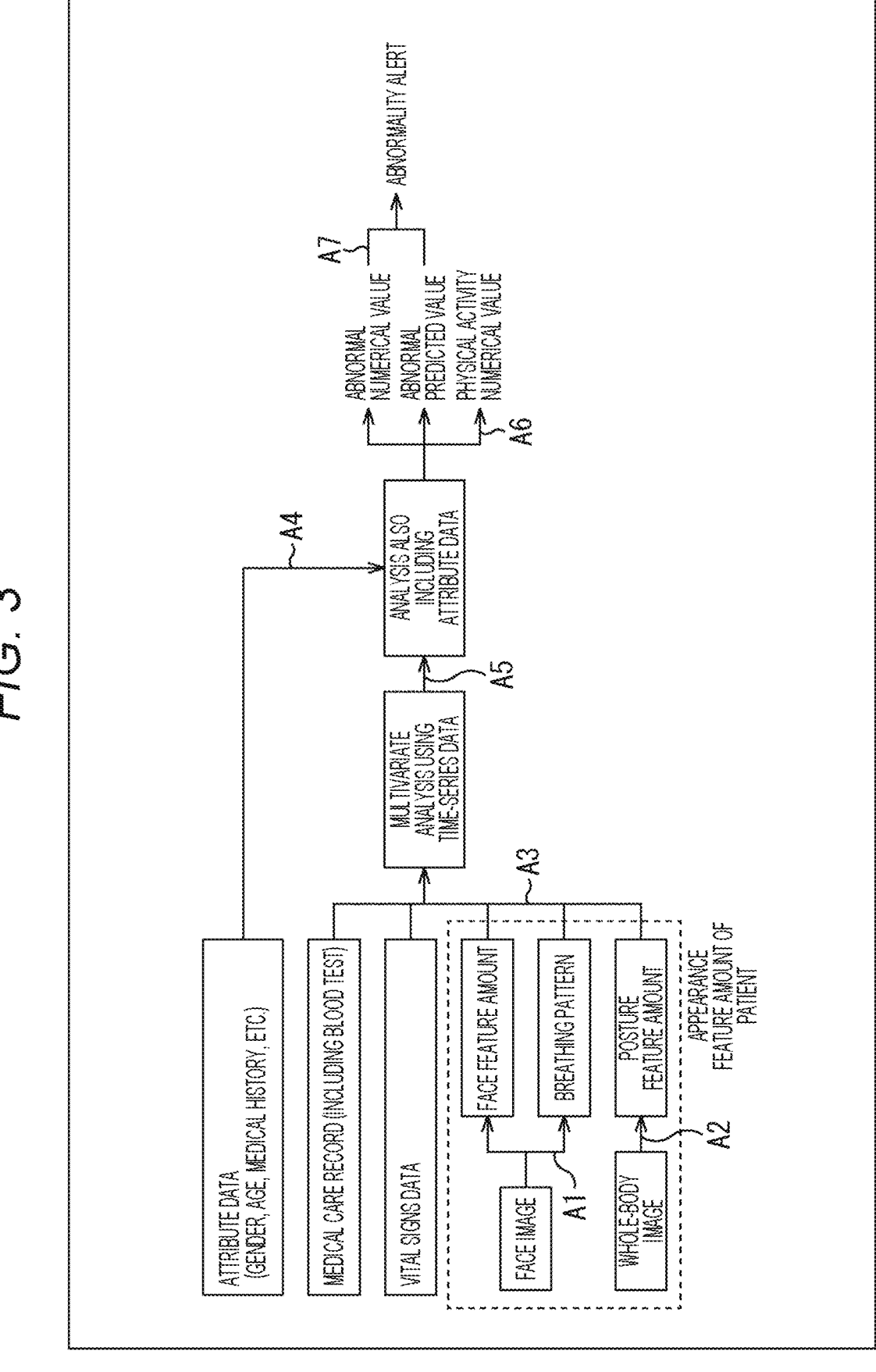
FIG. 3 is a diagram illustrating a flow of processing performed by the information processing apparatus.

FIG. 3 is a diagram illustrating a flow of processing performed by the information processing apparatus 3.

As indicated by an arrow A1 in FIG. 3, the information processing apparatus 3 extracts the face feature amount and the breathing pattern from the face image. For example, a numerical value indicating a writhing state based on the facial expression of the patient is extracted from the face image as the face feature amount. Furthermore, for example, a numerical value indicating a breathing state based on movement of muscles of the patient's mouth, nose, throat, and neck is extracted from the face image as a breathing pattern.

Patients in the ICU often wear a ventilator. Since the ventilator hides a part of the face of the patient, if a general-purpose facial expression detection technology is used to extract the face feature amount, the accuracy of facial expression detection may deteriorate.

Therefore, the information processing apparatus 3 performs facial expression recognition specialized for extraction of the feature amount around the patient's eye as the face feature amount.

Figure 4:
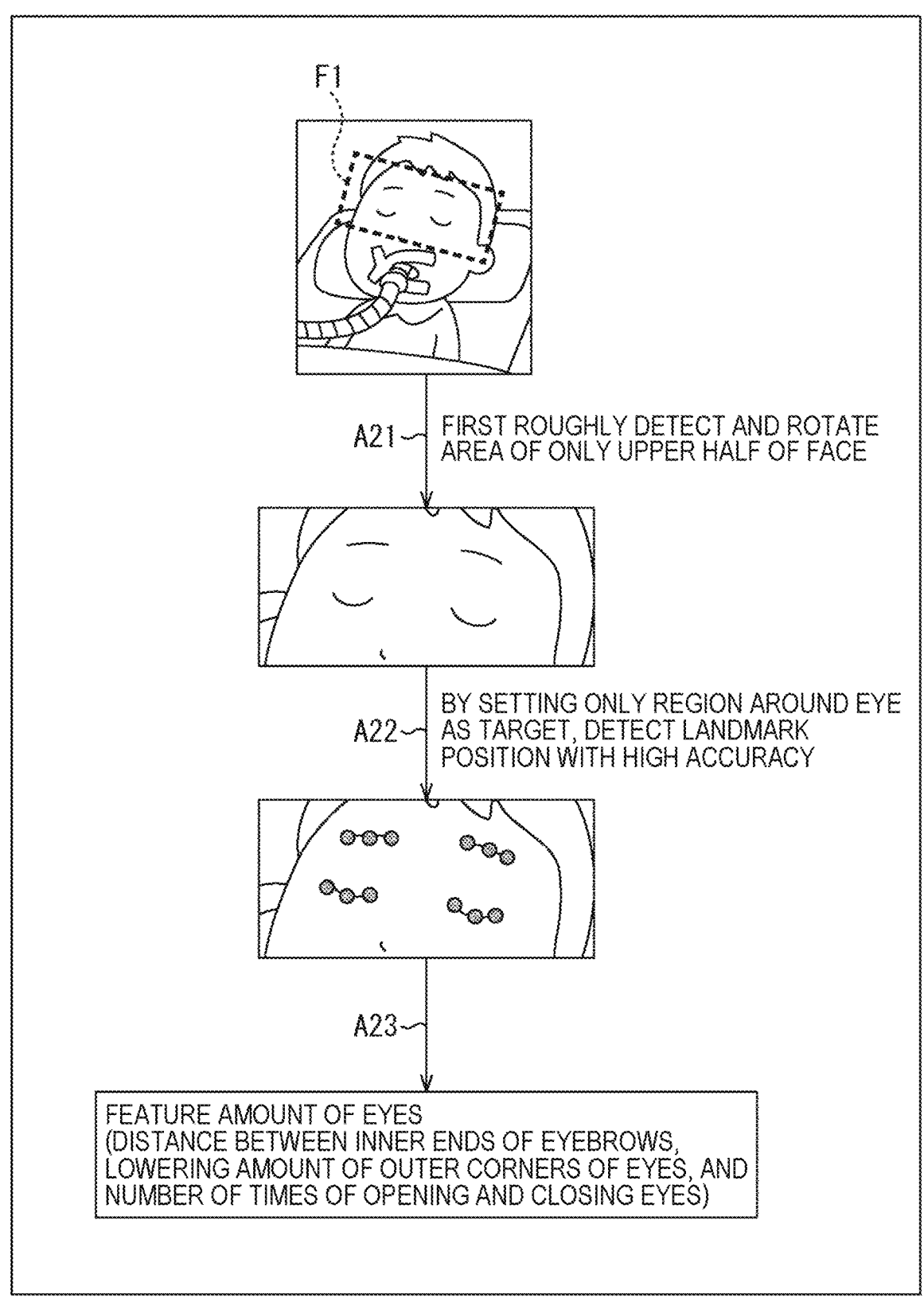
FIG. 4 is a diagram illustrating a flow of a method of extracting feature amounts around eyes.

FIG. 4 is a diagram illustrating a flow of a method of extracting a feature amount around the eye.

As indicated by an arrow A21 in FIG. 4, the information processing apparatus 3 roughly detects a region showing the upper half of the patient's face from the face image. In the example of FIG. 4, as illustrated in a rectangular frame F1, a region around the eye surrounding from the nose to the forehead of the patient is detected as a region used for feature amount extraction around the eye.

The information processing apparatus 3 cuts out a region around the eyes from the face image to generate a partial image. After rotating the partial image around the eye, the information processing apparatus 3 detects landmarks around the eye from the image as indicated by an arrow A22. For example, at least one of the position of the edge of the eyelid, the center position of the eye (the center position of the iris), the position of the eyebrow, the position of the inner corner of the eye, the position of the outer corner of the eye, or the position of the ridge of the nose is detected as the position of the landmark around the eye. The gray dots on the partial image around the eye indicate the locations of the landmarks around the eye.

By setting only the region around the eye as a target of landmark detection, it is possible to detect the landmark with high accuracy without being affected by the ventilator.

As indicated by an arrow A23, the information processing apparatus 3 extracts feature amounts around the eyes such as a distance between the inner ends of the eyebrows, an opening state of the eyelids, the number of times of opening and closing the eyelids, a lowering amount of the outer corners of the eyes, and a direction of the eye lines, for example, on the basis of the positions of the landmarks around the eyes. The feature amount around these eyes is a numerical value indicating the patient's suffering, depression, vigor, and the like. Note that information indicating a relative positional relationship between landmarks around the eye may be used as the feature amount around the eye.

In this manner, the information processing apparatus 3 can handle the sedation state, the painful expression, the consciousness state, the sleep state, and the like of the patient as numerical values. The information processing apparatus 3 records the feature amount around the eye extracted from the face image. Since not the face image itself but the feature amount around the eye is recorded, it is possible to realize a patient monitoring system in consideration of patient privacy.

Returning to FIG. 3, as indicated by an arrow A2, the information processing apparatus 3 extracts the posture feature amount from the whole-body image. For example, a numerical value indicating an excited state based on the spasm or movement of the patient's body is extracted from the whole-body image as the posture feature amount.

A patient in the ICU may be covered with futon bedding. Since the futon conceals a part of the patient's body, if a general-purpose skeleton estimation technique is used to extract the posture feature amount, the accuracy of skeleton estimation may be deteriorated.

Therefore, the information processing apparatus 3 performs recognition specialized for extraction of feature amounts of the face and the shoulder of the patient.

Figure 5:
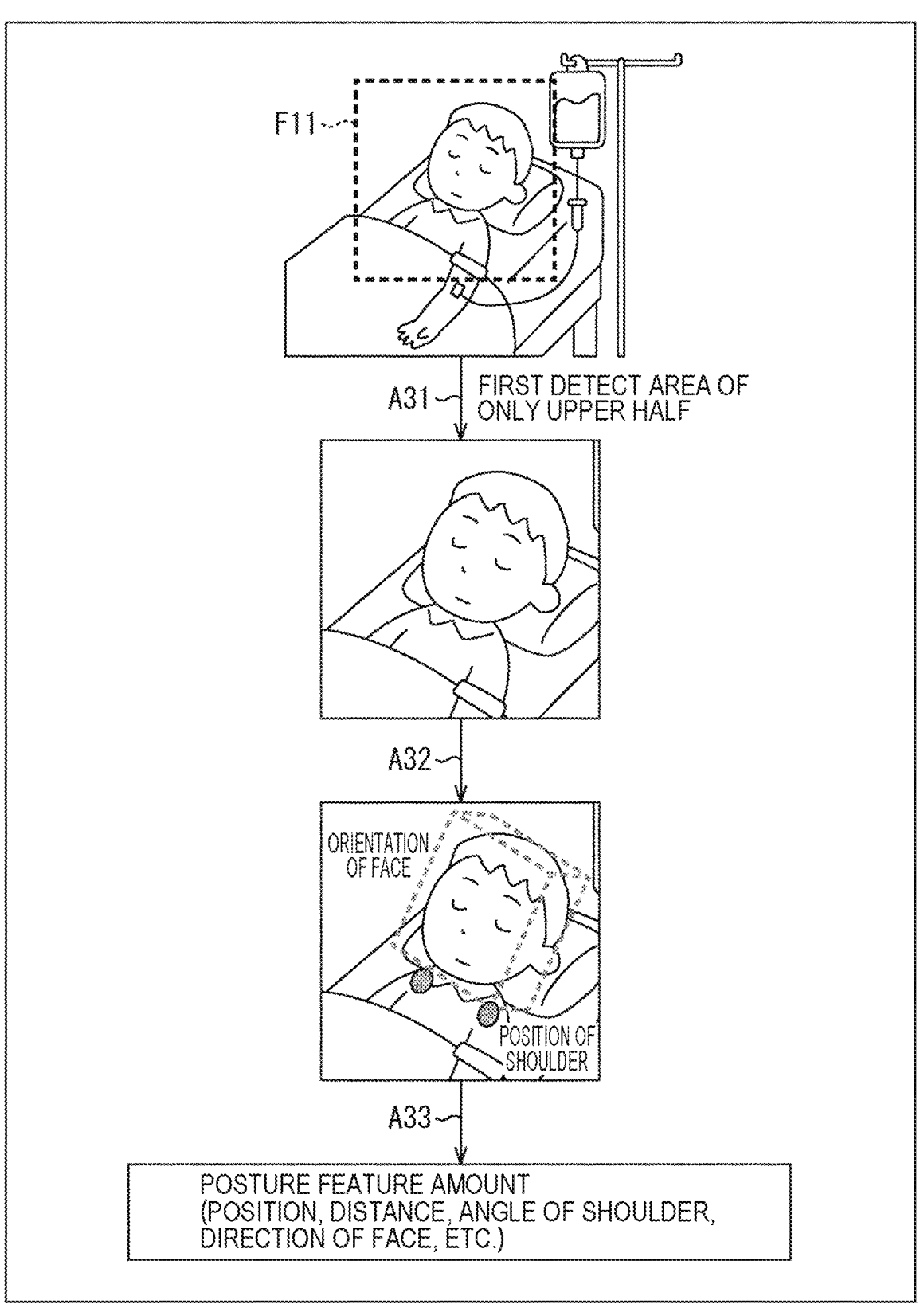
FIG. 5 is a diagram illustrating a flow of a method of extracting feature amounts of a face and a shoulder.

FIG. 5 is a diagram illustrating a flow of a method of extracting feature amounts of the face and the shoulder.

As indicated by an arrow A31 in FIG. 5, the information processing apparatus 3 roughly detects a region showing the upper body of the patient from the whole-body image. In the example of FIG. 5, a region surrounded by a rectangular frame F11 is detected as a region used for extraction of feature amounts of the face and the shoulder.

The information processing apparatus 3 cuts out a region of the upper body from the whole-body image to generate a partial image. After generating the partial image of the upper body, the information processing apparatus 3 detects the orientation of the face and the position of the shoulder from the partial image of the upper body as indicated by an arrow A32. A dashed square on the partial image of the upper body indicates the orientation of the face of the patient. Furthermore, two gray ellipses indicate the position of the shoulder.

By setting only the region of the upper body as the target of the detection of the position of the shoulder, the position of the shoulder can be detected with high accuracy without being affected by the futon.

As indicated by an arrow A33, the information processing apparatus 3 extracts the position of the shoulder, the distance between the shoulders, the angle between the shoulders, the direction of the face, and the like as the posture feature amount. Specifically, on the basis of the position of the shoulder and the orientation of the face, numerical values such as an angle at which the body rotates leftward with reference to the supine state, an angle at which the face tilts with reference to the shoulder, and an angle at which the right shoulder rises with reference to the left shoulder are obtained as the posture feature amount.

In this manner, the information processing apparatus 3 can handle the sedation state, the consciousness state, the sleep state, and the like of the patient as numerical values. The information processing apparatus 3 records the posture feature amount extracted from the whole-body image. Since the posture feature amount is recorded instead of the whole-body image, it is possible to realize a patient monitoring system in consideration of patient privacy.

As indicated by a broken line in FIG. 3, the face feature amount, the breathing pattern, and the posture feature amount extracted from the video as described above are used as the appearance feature amount of the patient for subsequent analysis.

As indicated by an arrow A3, the information processing apparatus 3 performs multivariate analysis using time-series data of appearance feature amounts obtained from videos of a predetermined period, in addition to medical care data and vital signs data.

Figure 6:
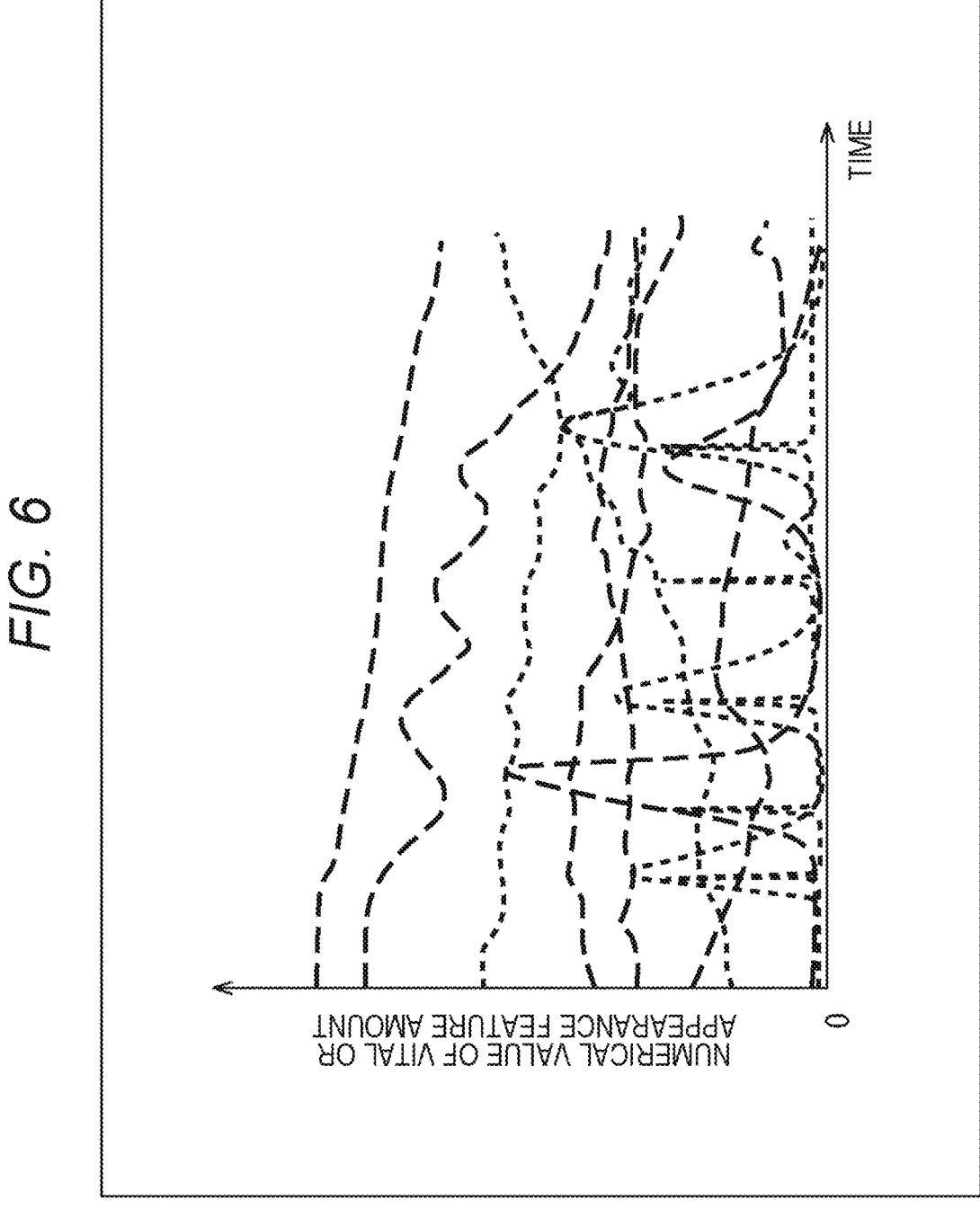
FIG. 6 is a diagram illustrating an example of time-series data used for multivariate analysis.

FIG. 6 is a diagram illustrating an example of time-series data used for multivariate analysis. In FIG. 6, a horizontal axis represents time, and a vertical axis represents a numerical value of a vital sign or an appearance feature amount.

As illustrated in FIG. 6, time-series data of a result of a blood test performed in a predetermined period, time-series data of vital signs detected in the predetermined period, and time-series data of appearance feature amounts extracted from frame images constituting a video of the predetermined period are used for multivariate analysis.

Note that, in a case where the sampling rates of the vital sign, the frame image, the blood test result, and the like are different from each other, the information processing apparatus 3 performs interpolation processing, and generates the vital sign, the appearance feature amount (frame image), the blood test result, and the like at the same time. The time-series data after the interpolation processing is used for multivariate analysis.

The multivariate analysis is performed using a method such as principal component analysis, machine learning, or deep learning. For example, by inputting the medical care data, the vital sign data, and the time-series data of the appearance feature amount, the predicted value of the vital sign after a predetermined time from the reference time is output from the learning model. As an example of the reference time, the time when the frame image is captured, the time when the vital sign is detected, or the time when the blood test is performed can be considered. As the predicted value of the vital sign, for example, blood pressure, SpO2, heart rate, and breathing rate after a predetermined time are estimated by multivariate analysis. Furthermore, the probability of blood pressure decrease, the probability of SpO2, the probability of heart rate increase, and the probability of breathing rate increase may be estimated by multivariate analysis. Thus, the future condition of the patient is estimated by multivariate analysis.

After performing the multivariate analysis, as indicated by arrows A4 and A5 in FIG. 3, the information processing apparatus 3 performs analysis using the attribute data and the result of the multivariate analysis. This analysis is also performed using a method such as principal component analysis, machine learning, or deep learning.

Specifically, it is conceivable to perform processing of two patterns as the analysis using the attribute data and the result of the multivariate analysis.

In the processing of the first pattern, the predicted value of the vital sign after a predetermined time as a result of the multivariate analysis is corrected on the basis of the attribute data, and it is determined whether or not the corrected predicted value exceeds the threshold.

In the processing of the second pattern, the threshold is adjusted on the basis of the attribute data. After adjusting the threshold, a determination is made as to whether or not the predicted value of the vital sign after a predetermined time as a result of the multivariate analysis exceeds the adjusted threshold.

After performing the analysis using the attribute data and the result of the multivariate analysis, the information processing apparatus 3 displays an abnormal numerical value, an abnormal predicted value, a physical activity numerical value, and the like on the monitor 4 as indicated by an arrow A6. The abnormal numerical value is, for example, a value indicating the degree of risk when the vital sign changes suddenly or a probability that the vital sign changes suddenly. The abnormal predicted value is a predicted value exceeding a threshold. Furthermore, the physical activity amount numerical value is a value indicating the degree of movement of the patient at the time when the frame image was captured. The physical activity amount numerical value indicates that the patient is moving, tired, and the like. Information such as an abnormal numerical value, an abnormal predicted value, and a physical activity numerical value is obtained by analysis using attribute data and a result of multivariate analysis.

As indicated by an arrow A7, the information processing apparatus 3 controls the monitor 4 to issue an abnormality alert on the basis of the abnormal numerical value and the abnormal predicted value. For example, in a case where it is determined that the abnormal numerical value or the abnormal predicted value exceeds the threshold, the prediction time at which the vital sign changes suddenly and the type of the sudden change are displayed on the monitor 4, and an alert for warning a sudden change in the state of the patient is issued to the medical practitioner. As the type of the sudden change, for example, at least one of a decrease in blood pressure, a decrease in SpO2, an increase in heart rate, or an increase in breathing rate is displayed on the monitor 4.

Figure 7:
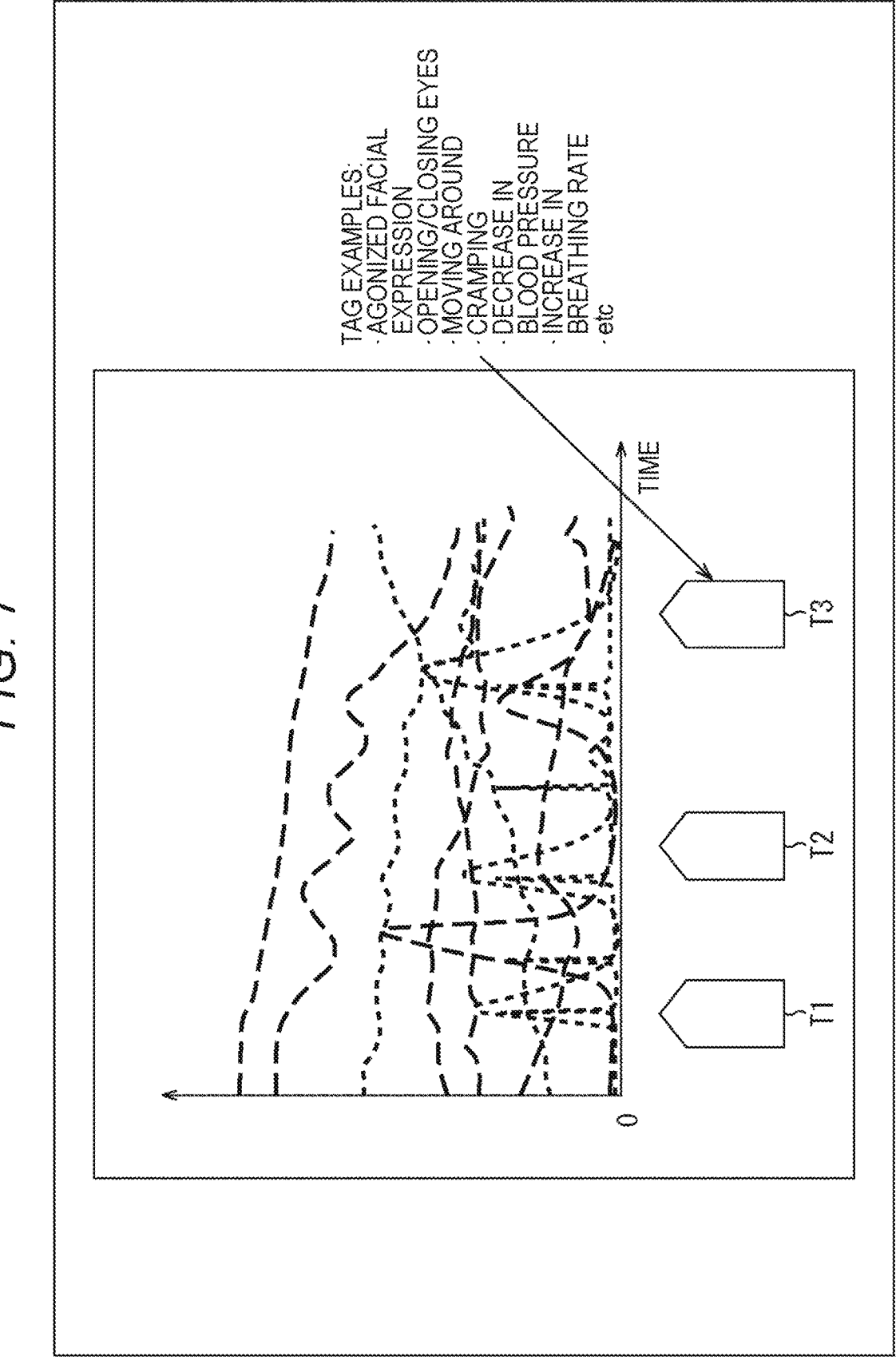
FIG. 7 is a diagram illustrating an example of a display screen.

FIG. 7 is a diagram illustrating an example of a display screen.

As illustrated on the left side of FIG. 7, the monitor 4 displays time-series data of vital signs and appearance feature amounts, and displays tags T1 to T3 on time series.

For example, the tag is set for the time at which a change in the patient's condition, such as the patient making an agonized facial expression, opening or closing eyes, moving around, or cramping, is detected on the basis of the appearance feature amount. Furthermore, the tag is also set for the time when a change in the patient's condition, such as a decrease in blood pressure or an increase in breathing rate, is detected on the basis of the vital sign.

The video captured around the time when the tag is set is recorded by the information processing apparatus 3. In a case where the tag is selected by the medical practitioner viewing the display on the monitor 4, the information processing apparatus 3 causes the monitor 4 to display a video showing the patient around the time when the tag is set. By selecting the tag, the medical practitioner can check the video around the time when the patient's condition has changed.

Since the video is recorded only when the condition of the patient changes, the storage capacity of the video data can be reduced. Furthermore, the medical practitioner can efficiently check the state of the patient around the time when the condition of the patient has changed without performing complicated operations such as checking the state of the patient by operating the timeline of the video.

Note that the tag may be set not only for the time at which the change in the patient's condition is detected but also for future time at which the vital sign is estimated to change suddenly on the basis of the analysis result by the information processing apparatus 3. The tag set for the future time is displayed on the monitor 4 together with the predicted value of the vital sign, for example.

In this manner, information indicating the current state of the patient, such as the vital sign and the time-series data of the appearance feature amount, and information indicating the future state of the patient, such as the predicted value of the vital sign and the alert, are displayed on the monitor 4.

As described above, the patient monitoring of the present technology can quantify the uncomfortable feeling empirically determined by the medical practitioner by looking at the appearance of the patient on the basis of the video showing the patient, display the quantified appearance feature amount, and predict the sudden change in the patient's condition on the basis of the appearance feature amount.

The medical practitioner can appropriately monitor a sign of sudden change in the state or condition of the patient by viewing the appearance feature amount of each patient displayed on the monitor 4 without checking the state of each patient. Therefore, it is possible to reduce frequent monitoring work of the medical practitioner. Furthermore, it is possible to prevent overlooking of an abnormality occurring in a patient.

Since the patient state is estimated on the basis of the video, the vital signs data, and the medical care data that are constantly acquired, the information processing apparatus 3 can constantly monitor the patient state such as 24 hours or 365 days.

Figure 8:
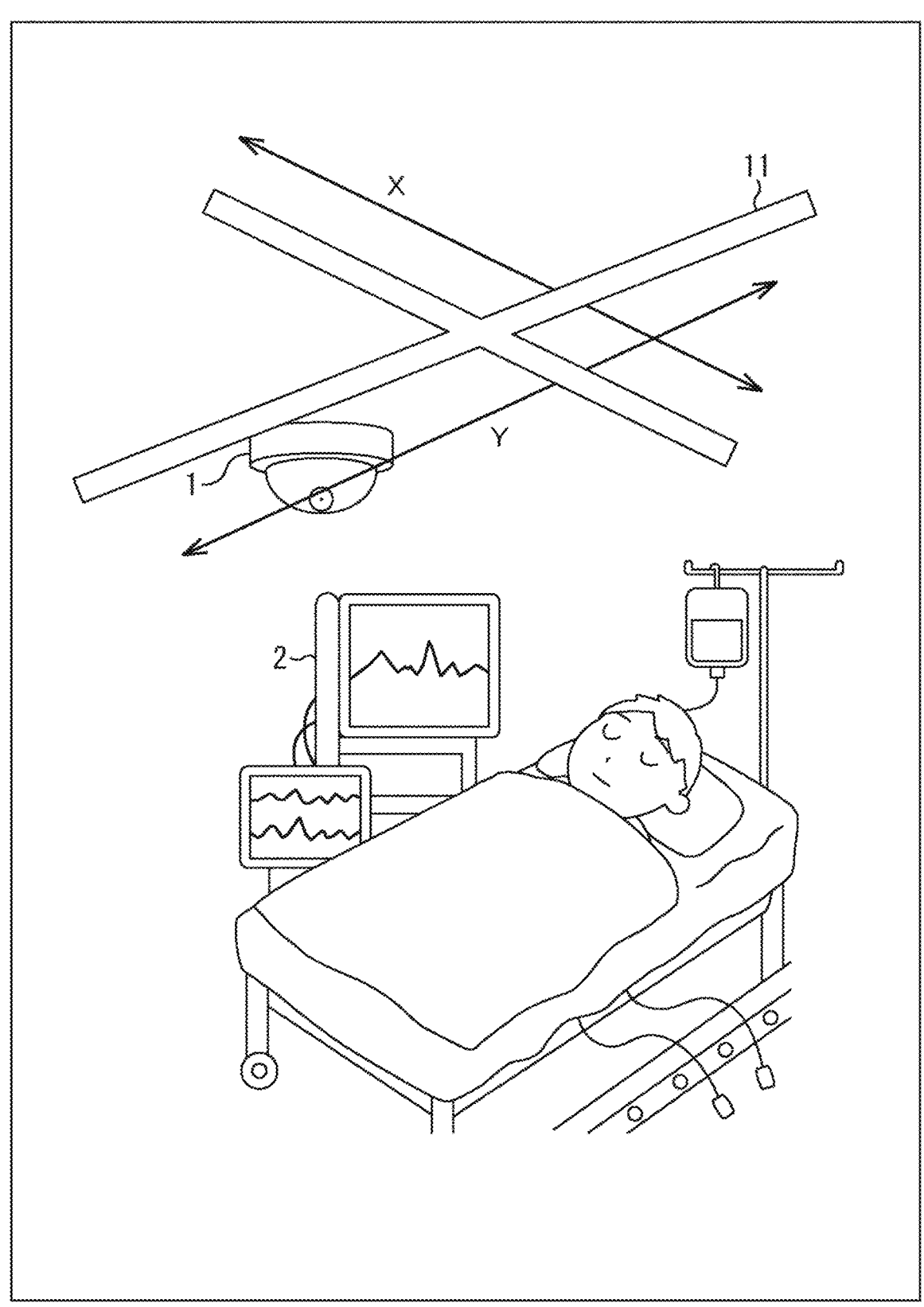
FIG. 8 is a diagram illustrating an arrangement example of a camera for each patient.

FIG. 8 is a diagram illustrating an arrangement example of the camera 1 for each patient.

As illustrated in the upper side of FIG. 8, a two-axis (X axis, Y axis) rail 11 is fixed to the ceiling in the vicinity of the bed used by the patient, and the camera 1 is provided on the rail 11. The camera 1 can change its position along the rail 11 as a moving mechanism. Note that the rail 11 may be fixed to a bed used by a patient.

For example, in the ICU, the patient's posture may change due to a change in reclining angle of the bed or a change in position. Since the posture of the patient changes, it is difficult to always image the face of the patient from the front. Therefore, in the patient monitoring system of the present technology, the camera 1 moves to a position where the face of the patient is imaged from the front. The position of the camera 1 is controlled by the information processing apparatus 3.

When the camera 1 captures an image of the face of the patient, the camera 1 first captures an image at a low magnification to acquire a video of the entire body of the patient viewed from above. The information processing apparatus 3 detects the position and orientation of the patient's face from the video acquired in this manner.

The information processing apparatus 3 moves the camera 1 to a position where the face of the patient can be imaged from a direction close to the front on the basis of the detection result of the position and orientation of the face of the patient. Next, the information processing apparatus 3 pans, tilts, and zooms the camera 1 so as to show the face of the patient.

By performing such control, a face image is acquired. Even if the reclining angle of the bed used by the patient changes, even if the posture of the patient changes to face up, right, left, or the like due to the change in position, the camera 1 is moved to a position where the face of the patient can be imaged from the front, and it is possible to acquire a video in which the face feature amount can be easily extracted.

Note that the rail 11 on which the camera 1 is provided can be one or more rails. Furthermore, the shape of the rail 11 may be a straight line or a curved line.

Figure 9:
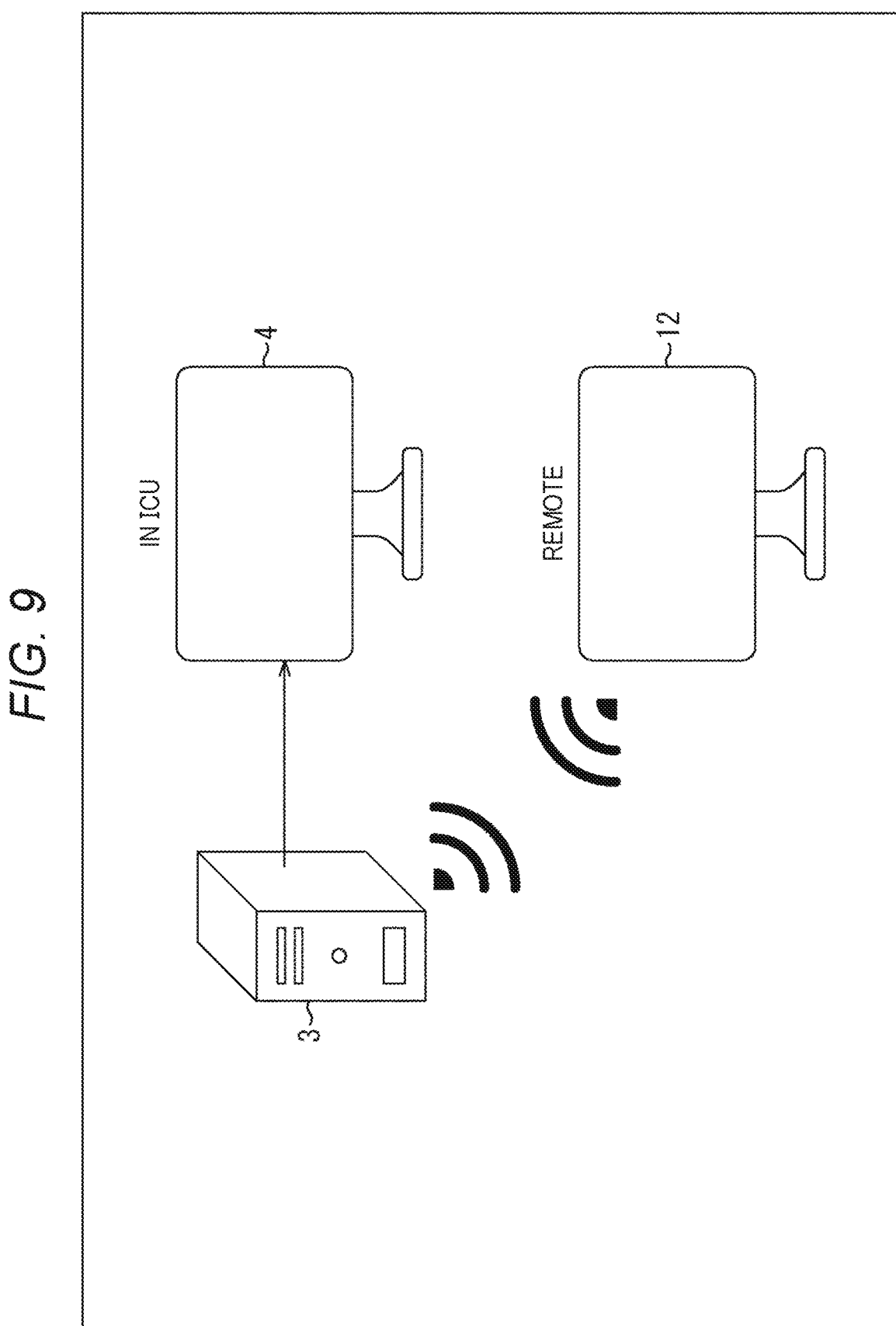
FIG. 9 is a diagram illustrating another configuration example of the patient monitoring system.

FIG. 9 is a diagram illustrating another configuration example of the patient monitoring system.

The patient monitoring system illustrated in FIG. 9 is configured by connecting a remote monitor 12 to the information processing apparatus 3 in addition to the monitor 4 in the ICU. The remote monitor 12 is connected to the information processing apparatus 3 via wireless communication, for example.

The remote monitor 12 is a monitor provided outside the ICU such as another hospital. The remote monitor 12 displays information similar to the information displayed on the monitor 4 under the control of the information processing apparatus 3. The remote medical practitioner can give instructions to the medical practitioner in the ICU while checking the predicted value of the patient's vital sign and the like displayed on the remote monitor 12.

In this manner, information indicating the state of each of the plurality of patients estimated in consideration of the appearance of the patient may be displayed in a list on a monitor provided outside the ICU.

2. Configuration of Information Processing Apparatus

Figure 10:
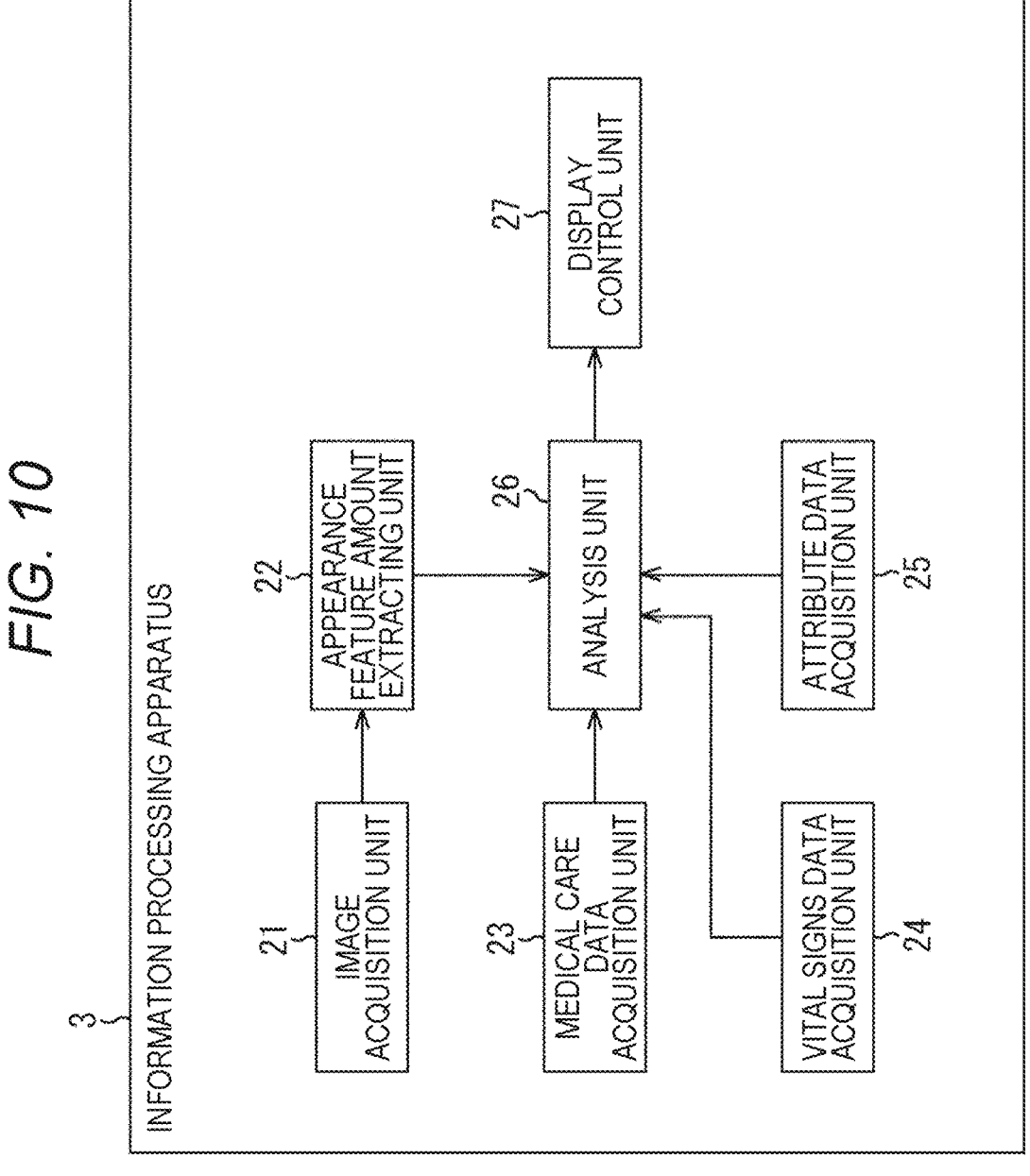
FIG. 10 is a block diagram illustrating a functional configuration example of the information processing apparatus.

FIG. 10 is a block diagram illustrating a functional configuration example of the information processing apparatus 3. Hereinafter, an example of monitoring the state of one patient will be described.

Actually, processing by each configuration of the information processing apparatus 3 is performed for each of a plurality of patients.

As illustrated in FIG. 10, the information processing apparatus 3 includes an image acquisition unit 21, an appearance feature amount extracting unit 22, a medical care data acquisition unit 23, a vital signs data acquisition unit 24, an attribute data acquisition unit 25, an analysis unit 26, and a display control unit 27.

The image acquisition unit 21 acquires a video showing the patient from the camera 1. Furthermore, the image acquisition unit 21 controls the position, direction, and angle of view of the camera 1 on the basis of the video acquired from the camera 1. A frame image constituting a video showing the patient is output to the appearance feature amount extracting unit 22.

The appearance feature amount extracting unit 22 functions as an analysis unit that analyzes a video showing a patient and acquires video analysis information indicating an analysis result. As the video analysis information, for example, the appearance feature amount is extracted from the frame image supplied from the image acquisition unit 21.

Specifically, the appearance feature amount extracting unit 22 detects a region from which the appearance feature amount is extracted from the frame image. For example, the appearance feature amount extracting unit 22 detects a region around the patient's eye and a region of the upper body of the patient from the frame image. The appearance feature amount extracting unit 22 extracts the face feature amount and the posture feature amount as the appearance feature amount from the detected region.

The time-series data of the appearance feature amount extracted by the appearance feature amount extracting unit is supplied to the analysis unit 26.

The medical care data acquisition unit 23 communicates with other systems and the like in the ICU and acquires medical care data for the patient. The medical care data acquired by the medical care data acquisition unit 23 is output to the analysis unit 26.

The vital signs data acquisition unit 24 acquires the vital sign data of the patient from the medical device 2 and outputs the vital sign data to the analysis unit 26.

The attribute data acquisition unit 25 communicates with other systems in the ICU, other systems in the hospital, and the like, and acquires attribute data regarding the patient. The attribute data acquired by the attribute data acquisition unit 25 is output to the analysis unit 26.

The analysis unit 26 performs multivariate analysis using time-series data of appearance feature amounts, medical care data, and vital signs data. Specifically, the time-series data of the appearance feature amount, the medical care data, and the vital sign data are input to the learning model, and the predicted value of the vital sign after a predetermined time is output. Note that, in a case where the sampling rates of the appearance feature amount, the blood test result, and the vital sign are different from each other, the analysis unit 26 performs the interpolation processing such that the sampling rate of the information with a low sampling rate among the appearance feature amount, the blood test result, and the vital sign is adjusted to the sampling rate of the information with the highest sampling rate, and then performs the multivariate analysis. The analysis unit 26 functions as an interpolation unit that performs interpolation processing on information with a low sampling rate.

The analysis unit 26 further performs analysis using the result of the multivariate analysis and the attribute data. Specifically, the predicted value and the attribute data of the vital sign after a predetermined time are input to the learning model, and a determination result as to whether or not the vital sign changes suddenly is output. Together with this determination result, an abnormal numerical value, an abnormal predicted value, a physical activity amount numerical value, and the like are also output.

FIG. 11 is a diagram illustrating an example of a learning data set of a learning model used for each analysis.

The learning data set illustrated in A of FIG. 11 includes time-series data of the vital sign, the face feature amount, and the posture feature amount as input data, and includes time-series data of the vital sign as output data.

As described above, the learning model used in the multivariate analysis using the time-series data is generated by machine learning using the time-series data of the vital sign, the face feature amount, and the posture feature amount labeled with the time-series data of the vital sign indicating the state of the patient as the learning data.

In the learning data set illustrated in B of FIG. 11, a predicted value of the vital sign and attribute data are included as input data, and a value to be corrected for the predicted value of the vital sign is included as output data. For example, the difference between the predicted value and the measured value of the vital sign is used as a value to be corrected for the predicted value.

As described above, the learning model used in the analysis using the result of the multivariate analysis and the attribute data is generated by machine learning using the attribute data in which the difference between the predicted value of the vital sign and the measured value is labeled and the predicted value as the result of the multivariate analysis as learning data. The learning model used in the multivariate analysis and the learning model used in the analysis using the result of the multivariate analysis and the attribute data are configured as long short-term memory (LSTM), for example.

Returning to FIG. 10, the analysis unit 26 outputs the result of the multivariate analysis and the result of the analysis using the attribute data to the display control unit 27. The analysis unit 26 also functions as an estimation unit that inputs the time-series data of the appearance feature amount, the vital signs data, and the like to the learning model to estimate the state of the patient.

The display control unit 27 causes the monitor 4 to display information indicating the state of the patient. For example, analysis results by the analysis unit 26, time-series data of appearance feature amounts, medical care data, vital signs data, and attribute data are displayed on the monitor 4 as information indicating the state of the patient. In this case, the same data as the time-series data of the appearance feature amount supplied to the analysis unit 26, the medical care data, the vital signs data, and the attribute data is supplied to the display control unit 27.

Furthermore, the display control unit 27 issues an alert or the like according to the analysis result by the analysis unit 26 to provide notification that a sudden change in the vital sign of the patient is predicted. The display control unit 27 functions as a monitoring unit that monitors the state of the patient on the basis of the analysis result by the analysis unit 26.

3. Operation of Information Processing Apparatus

Figure 12:
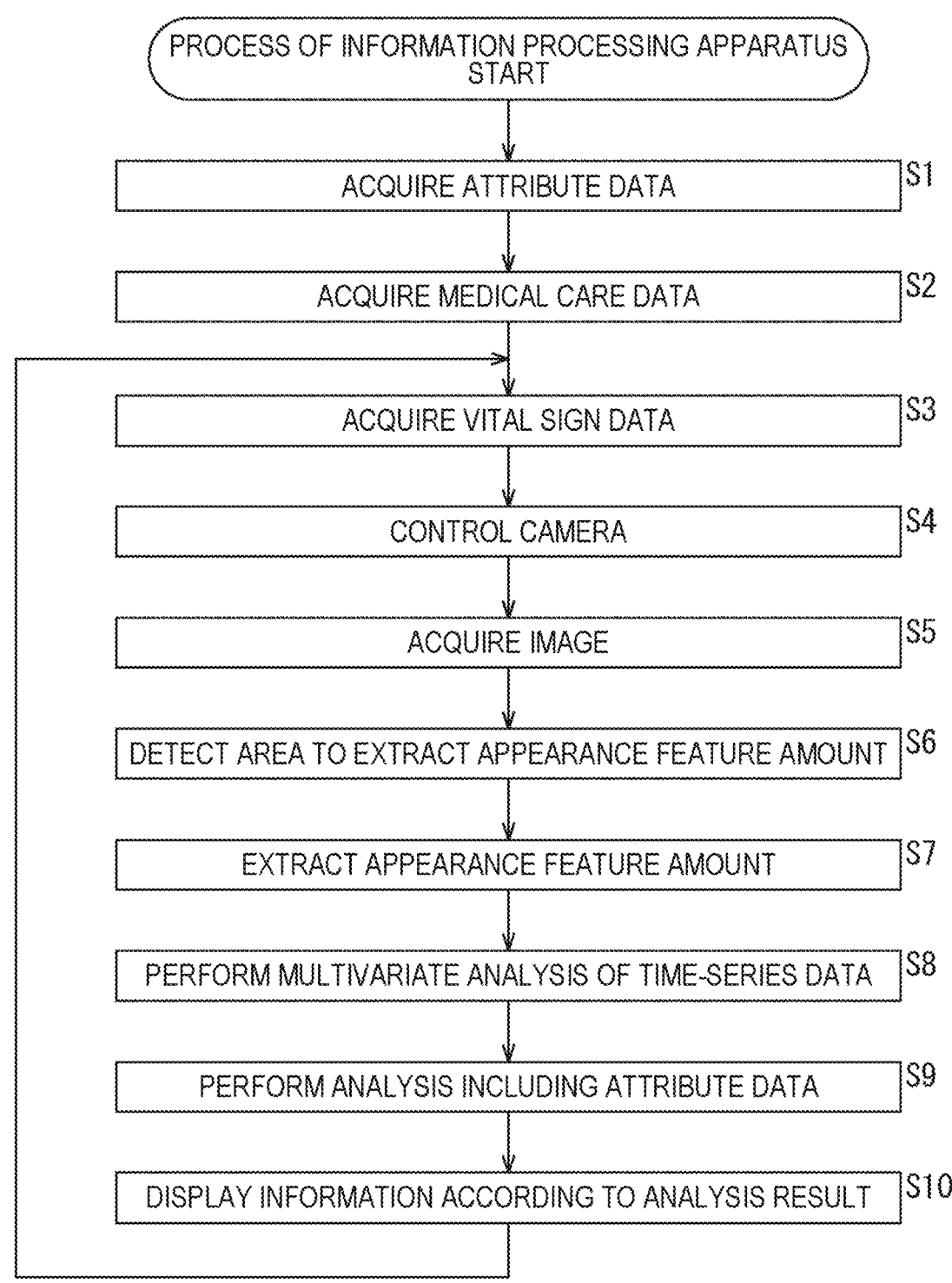
FIG. 12 is a flowchart for explaining processing of the information processing apparatus.

With reference to a flowchart of FIG. 12, processing of the information processing apparatus 3 will be described.

In step S1, the attribute data acquisition unit 25 acquires attribute data regarding the patient from another system in the ICU, another system in the hospital, or the like.

In step S2, the medical care data acquisition unit 23 acquires the medical care data from another system or the like in the ICU.

In step S3, the vital signs data acquisition unit 24 acquires the time-series data of the vital signs detected by the medical device 2 as vital signs data.

In step S4, the image acquisition unit 21 controls the position, direction, and angle of view of the camera 1.

In step S5, the image acquisition unit 21 acquires, from the camera 1, a frame image constituting a video showing the patient.

In step S6, the appearance feature amount extracting unit 22 detects a region from which the appearance feature amount is extracted from the frame image.

In step S7, the appearance feature amount extracting unit 22 extracts the appearance feature amount from the detected region.

In step S8, the analysis unit 26 performs multivariate analysis using the time-series data of the appearance feature amount, the vital signs data, and the medical care data.

In step S9, the analysis unit 26 performs analysis using a result of multivariate analysis and attribute data.

In step S10, the display control unit 27 causes the monitor 4 to display information indicating the state of the patient according to the analysis result by the analysis unit 26.

After the information indicating the state of the patient is displayed on the monitor 4, the process returns to step S3, and the subsequent processes are repeatedly performed. Note that, in a case where the medical care data is updated such that the blood test is performed again, the updated medical care data is appropriately acquired by the medical care data acquisition unit 23.

As described above, the medical practitioner can appropriately monitor a sign of sudden change in the state or condition of the patient by viewing the appearance feature amount of each patient displayed on the monitor 4 without checking the state of each patient.

4. Modifications

A sampling rate such as a frame image, a vital sign, and a blood test result may be set according to the severity of the patient. Therefore, this can minimize the overall processing cost of the patient monitoring system.

The camera 1 may include a night-vision camera. The appearance feature amount may be extracted from a video captured by a depth sensor, a video captured by receiving light in a short wavelength infra-red (SWIR) wavelength band, or a video captured by a thermo camera.

Time-series data of patient sensing information acquired using an electromagnetic wave such as a millimeter wave may be used for analysis by the information processing apparatus 3. For example, time-series data of sensing information indicating a heartbeat or respiration of a patient acquired using an electromagnetic wave is used for analysis as vital sign data. Furthermore, the time-series data of the sensing information indicating the posture of the patient acquired using the electromagnetic wave is used for analysis as the time-series data of the appearance feature amount.

By the analysis using the result of the multivariate analysis and the attribute data, not only it is determined whether or not a sudden change in vital signs such as a decrease in blood pressure, a decrease in SpO2, an increase in heart rate, and an increase in breathing rate occurs, but also it may be determined whether or not an event such as intervention by a medical practitioner or a patient pressing a nurse call occurs.

The learning model used for prediction of occurrence of an event is generated by machine learning using a learning data set including attribute data and a predicted value of a vital sign as a result of multivariate analysis, in which information indicating an occurrence situation of an event such as intervention of a medical practitioner is labeled.

The multivariate analysis may be performed by using a plurality of learning models that output respective predicted values of the blood pressure, SpO2, the heart rate, and the breathing rate after a predetermined time. In this case, a list of predicted values of the blood pressure, SpO2, the heart rate, and the breathing rate after a predetermined time output from each of the plurality of learning models is displayed on the monitor 4.

An integrated feature amount that is a feature amount obtained by integrating the time-series data of the appearance feature amount, the vital sign data, and the medical care data may be extracted by the learning model used in the multivariate analysis. In this case, in the analysis using the attribute data, the integrated feature amount and the attribute data are input to the learning model, and a determination result as to whether or not the state of the patient changes suddenly is output.

When the predicted value of the vital sign (result of multivariate analysis) exceeds a threshold, not only an alert may be issued, but also an alert may be issued on the basis of statistics of the predicted value of the vital sign. For example, in consideration of the time-series change in the predicted value of the vital sign, an alert indicating that the predicted value of the vital sign gradually approaches the threshold is issued.

Computer

The series of processing described above can be executed by hardware or by software. In a case where the series of processes is executed by software, a program included in the software is installed from a program recording medium to, for example, a computer incorporated in dedicated hardware, or a general-purpose personal computer.

Figure 13:
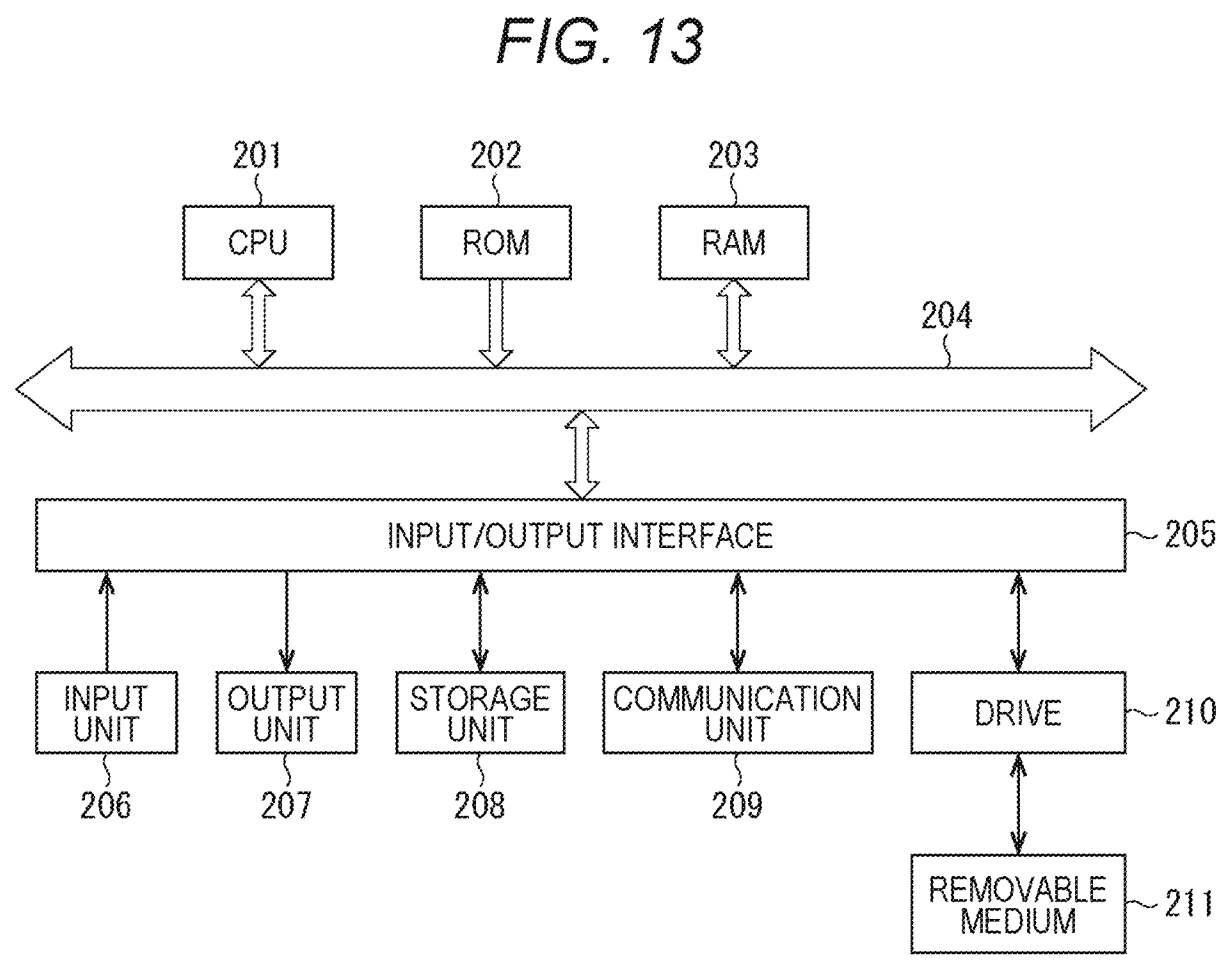

FIG. 13 is a block diagram illustrating a configuration example of hardware of a computer that executes the above-described series of processes by a program.

A central processing unit (CPU) 201, a read only memory (ROM) 202, and a random access memory (RAM) 203 are mutually connected by a bus 204.

An input/output interface 205 is further connected to the bus 204. An input unit 206 including a keyboard, a mouse, and the like, and an output unit 207 including a display, a speaker, and the like are connected to the input/output interface 205. Furthermore, the input/output interface 205 is connected to a storage unit 208 including a hard disk, a non-volatile memory, or the like, to a communication unit 209 including a network interface or the like, and to a drive 210 that drives a removable medium 211.

In the computer configured in the above-described manner, the CPU 201 loads the program stored in the storage unit 208 on the RAM 203 through the input/output interface 205 and the bus 204 to execute, for example, and according to this, the above-described series of processes is performed.

The program executed by the CPU 201 is provided, for example, by being recorded in the removable medium 211 or via a wired or wireless transmission medium such as a local area network, the Internet, or digital broadcasting, and is installed in the storage unit 208.

Note that the program executed by the computer may be a program for processing in time series in the order described in the present description, or a program for processing in parallel or at a necessary timing such as when a call is made.

Others

Note that in the present Description, a system means a set of a plurality of constituents (devices, modules (components), or the like), and it does not matter whether or not all the constituents are in the same case. Therefore, a plurality of devices housed in separate housings and connected via a network and one device in which a plurality of modules is housed in one housing are both systems.

Note that the effects described in the present Description are merely examples and are not limited, and other effects may be provided.

The embodiments of the present technology are not limited to the above-described embodiments, and various modifications can be made without departing from the gist of the present technology.

For example, the present technology may be configured as cloud computing in which a function is shared by a plurality of devices through the network to process together. The plurality of devices is, for example, an IP converter, an IP switcher, or a server. For example, a configuration may be employed in which a feature amount is extracted from a signal output from a camera or a medical device to which each IP converter is connected, and a server aggregates and analyzes the feature amounts from each IP converter to estimate the patient state.

Furthermore, each step described in the above-described flowchart can be executed by one device or executed by a plurality of devices in a shared manner.

Moreover, in a case where a plurality of processes is included in one step, the plurality of processes included in one step can be executed by one device or by a plurality of devices in a shared manner.

Examples of Combinations of Configurations

The present technology can also employ the following configurations:

(1)

A patient monitoring system including:

an estimation unit that inputs vital information indicating a vital sign of a patient and video analysis information obtained by analyzing a video showing the patient to a first learning model to estimate a state of the patient; and a monitoring unit that monitors a state of the patient on the basis of an estimation result by the estimation unit.

(2)

The patient monitoring system according to (1), in which the vital information is time-series data of a predetermined period.

(3)

The patient monitoring system according to (1) or (2), in which the video analysis information is time-series data of a feature amount of an appearance of the patient extracted from the video of a predetermined period.

(4)

The patient monitoring system according to (3), in which the feature amount includes at least one of a face feature amount, a breathing pattern, or posture information.

(5)

The patient monitoring system according to (1) to (4), in which the first learning model is a machine learning model generated by learning using learning data including the vital information in which a state of the patient is labeled and the video analysis information.

(6)

The patient monitoring system according to (1) to (4), in which the first learning model is a machine learning model generated by learning using learning data including the vital information labeled as presence or absence of intervention by a medical practitioner and the video analysis information.

(7)

The patient monitoring system according to (1) to (6), in which the estimation unit estimates a future state of the patient.

(8)

The patient monitoring system according to (4), in which the face feature amount is a numerical value based on a position of a landmark of an eye of the patient in the video or a position of a landmark of an eye of the patient.

(9)

The patient monitoring system according to (4), in which the video analysis information is information indicating a direction of a face of the patient and positions of both shoulders, or a numerical value based on the direction of a face of the patient and the positions of both shoulders.

(10)

The patient monitoring system according to any one of (1) to (9), in which the estimation unit inputs attribute data including at least one of gender, age, or medical history of the patient and an output result of the first learning model to a second learning model to estimate a state of the patient.

(11)

The patient monitoring system according to any one of (1) to (10), in which the estimation unit inputs medical care data of the patient to the first learning model together with the vital information and the video analysis information to estimate a state of the patient.

(12)

The patient monitoring system according to any one of (1) to (11), in which the first learning model is an LSTM.

(13)

The patient monitoring system according to any one of (1) to (12), in which the monitoring unit provides notification of a sudden change in a state of the patient on the basis of an estimation result by the estimation unit.

15

(14)

The patient monitoring system according to (13), in which the monitoring unit displays information including a probability that a state of the patient suddenly changes.

(15)

The patient monitoring system according to any one of (1) to (14), in which the first learning model outputs at least one of a probability of blood pressure decrease, a probability of SpO2 decrease, a probability of heart rate increase, or a probability of breathing rate increase after a predetermined time from a time at which a frame image of the video is captured.

(16)

The patient monitoring system according to any one of (1) to (15), in which the estimation unit inputs the vital information and the video analysis information to a plurality of the first learning models that respectively output different types of information indicating the state of the patient to estimate a state of the patient, and the monitoring unit displays a list of the different types of information.

(17)

The patient monitoring system according to (13), in which the monitoring unit provides notification that a state of the patient suddenly changes on the basis of statistics of an output result of the first learning model.

(18)

The patient monitoring system according to any one of (1) to (17), further including an interpolation unit that performs interpolation processing on information having a low sampling rate in a case where a sampling rate of the vital information is different from a sampling rate of the video analysis information.

(19)

The patient monitoring system according to any one of (1) to (18), in which the monitoring unit generates a tag on the basis of a state of the patient, and displays the tag in association with future time estimated by the estimation unit that a sudden change in the state of the patient occurs.

(20)

The patient monitoring system according to (10), in which the first learning model outputs an integrated feature amount obtained by integrating the vital information and the video analysis information, and the second learning model receives the integrated feature amount and the attribute data as inputs and outputs information indicating a state of the patient.

(21)

The patient monitoring system according to any one of (1) to (20), further including a control unit that controls a position, an orientation, and an angle of view of a camera that captures the video on the basis of the video.

REFERENCE SIGNS LIST

1 Camera
2 Medical device
3 Information processing apparatus
4 Monitor
11 Rail
12 Remote monitor
21 Image acquisition unit

16

22 Appearance feature amount extracting unit
23 Medical care data acquisition unit
24 Vital signs data acquisition unit
25 Attribute data acquisition unit
26 Analysis unit
27 Display control unit

The invention claimed is:

1. A patient monitoring system comprising:

circuitry that:

inputs vital information indicating a vital sign of a patient and video analysis information to a first learning model, the video analysis information obtained by analyzing a video showing the patient;

execute the first learning model to estimate a state of the patient based on the vital information and the video analysis information; and monitor that monitors the state of the patient on a basis of the estimated state of the patient, wherein the circuitry performs interpolation processing on information having a low sampling rate in a case where a sampling rate of the vital information is different from a sampling rate of the video analysis information.

2. The patient monitoring system according to claim 1, wherein the vital information is time-series data of a predetermined period.

3. The patient monitoring system according to claim 1, wherein the video analysis information is time-series data of a feature amount of an appearance of the patient extracted from the video of a predetermined period.

4. The patient monitoring system according to claim 3, wherein the feature amount includes at least one of a face feature amount, a breathing pattern, or posture information.

5. The patient monitoring system according to claim 1, wherein the first learning model is a machine learning model generated by learning using learning data including the vital information in which the state of the patient is labeled and the video analysis information.

6. The patient monitoring system according to claim 1, wherein the first learning model is a machine learning model generated by learning using learning data including the vital information labeled as presence or absence of intervention by a medical practitioner and the video analysis information.

7. The patient monitoring system according to claim 1, wherein the estimated state of the patient comprises a future state of the patient.

8. The patient monitoring system according to claim 4, wherein the at least one of the face feature amount, the breathing pattern, or the posture information comprises the face feature amount, and the face feature amount is a numerical value based on a position of a landmark of an eye of the patient in the video or a position of a landmark of an eye of the patient.

9. The patient monitoring system according to claim 4, wherein the at least one of the face feature amount, the breathing pattern, or the posture information comprises the posture information, and the posture information is information indicating a direction of a face of the patient and positions of both shoulders, or a numerical value based on the direction of a face of the patient and the positions of both shoulders.

10. The patient monitoring system according to claim 1, wherein the circuitry inputs attribute data including at least one of gender, age, or medical history of the patient and an output result of the first learning model to a second learning model to estimate the state of the patient.

11. The patient monitoring system according to claim 1, wherein the circuitry inputs medical care data of the patient to the first learning model together with the vital information and the video analysis information to estimate the state of the patient.

12. The patient monitoring system according to claim 1, wherein the first learning model is a Long Short-Term Memory (LSTM).

13. The patient monitoring system according to claim 1, wherein the monitor provides notification of a change in the state of the patient on a basis of the estimated state of the patient.

14. The patient monitoring system according to claim 13, wherein the monitor displays information including a probability that the estimated state of the patient changes.

15. The patient monitoring system according to claim 1, wherein the first learning model outputs at least one of a probability of blood pressure decrease, a probability of SpO2 decrease, a probability of heart rate increase, or a probability of breathing rate increase after a predetermined time from a time at which a frame image of the video is captured.

16. The patient monitoring system according to claim 1, wherein the first learning model is one of a plurality of first learning models, the circuitry inputs the vital information and the video analysis information to the plurality of first learning models that respectively output different types of information related to the state of the patient to estimate the state of the patient, and the monitor displays a list of the different types of information.

17. The patient monitoring system according to claim 13, wherein the monitor provides notification that the estimated state of the patient changes on a basis of statistics of an output result of the first learning model.

18. The patient monitoring system according to claim 1, wherein the monitor generates a tag on a basis of the state of the patient, and displays the tag in association with a future time estimated by the circuitry that a change in the state of the patient will occur.

19. The patient monitoring system according to claim 10, wherein the first learning model outputs an integrated feature amount obtained by integrating the vital information and the video analysis information, and the second learning model receives the integrated feature amount and the attribute data as inputs and outputs information indicating the estimated state of the patient.

20. A method performed by one or more components of a patient monitoring system, the method comprising:

inputting vital information indicating a vital sign of a patient and video analysis information to a first learning model to, the video analysis information obtained by analyzing a video showing the patient;

executing the first learning model to estimate a state of the patient based on the vital information and the video analysis information; and monitoring the state of the patient on a basis of the estimated state of the patient, wherein the method further comprises performing interpolation processing on information having a low sampling rate in a case where a sampling rate of the vital information is different from a sampling rate of the video analysis information.

\* \* \* \* \*